United States Patent [19]

Mason, Jr. et al.

[11] Patent Number: 4,886,513
[45] Date of Patent: Dec. 12, 1989

[54] ABSORBENT PAD WITH REINFORCING MEMBER TO RESIST DEFORMATION

[75] Inventors: Stanley I. Mason, Jr., Weston; Michael D. Handler, Norwalk, both of Conn.

[73] Assignee: Kimberly-Clark Corporation, Neenah, Wis.

[21] Appl. No.: 321,615

[22] Filed: Mar. 10, 1989

Related U.S. Application Data

[63] Continuation of Ser. No. 69,690, Jan. 6, 1987.

[51] Int. Cl.$^4$ .............................. A61F 13/16
[52] U.S. Cl. .................. 604/385.1; 604/358; 604/370
[58] Field of Search .............. 604/327, 346, 347, 354, 604/355, 358, 366, 367, 369, 370, 371, 372, 378, 385 R, 400

[56] References Cited

U.S. PATENT DOCUMENTS

| | | | |
|---|---|---|---|
| 2,551,663 | 5/1951 | Fox | 128/290 |
| 2,566,451 | 9/1951 | Julien | 128/290 |
| 2,731,014 | 1/1956 | Hollingsworth | 128/290 |
| 2,747,575 | 5/1956 | Mercer | 128/290 |
| 3,570,493 | 3/1971 | Olsson | 128/290 |
| 3,575,174 | 8/1971 | Mogor | 128/290 |
| 3,683,921 | 8/1972 | Brooks et al. | 128/296 |
| 3,736,931 | 6/1973 | Glassman | 128/290 R |
| 3,993,074 | 11/1976 | Murray et al. | 128/286 |
| 4,015,604 | 4/1977 | Csillag | 128/287 |
| 4,029,101 | 6/1977 | Chesky et al. | 128/290 R |
| 4,184,498 | 1/1980 | Franco | 128/290 R |
| 4,195,634 | 4/1980 | DiSalvo et al. | 128/290 R |
| 4,200,103 | 4/1980 | Black | 128/290 W |
| 4,389,211 | 6/1983 | Lenaghan | 604/383 |
| 4,505,705 | 3/1985 | Matthews et al. | 604/385 |
| 4,681,577 | 7/1987 | Stern et al. | 604/370 |
| 4,685,914 | 8/1987 | Hoffman | 604/368 |

FOREIGN PATENT DOCUMENTS

| | | |
|---|---|---|
| 2420339 | 3/1978 | France . |
| 2513115 | 8/1982 | France . |
| 814498 | 6/1959 | United Kingdom . |

OTHER PUBLICATIONS

International Publication, PCT/SE86/00426, International Publication #WO87/01914, Apr. 9, 1987; Hermansson, Jonas.

Primary Examiner—Noah P. Kamen
Attorney, Agent, or Firm—Thomas J. Connelly

[57] ABSTRACT

The invention is providing a flexibility stiff reinforcing member that will maintain the shape of a pad for absorption of human exudate, such as a feminine hygiene pad, during use. The flexibly stiff reinforcing member will return the pad to its desired shape, even after it has been deformed by movement of the wearer. In a particularly preferred form, the flexibly stiff reinforcing member is a flat strip of polyethylene that extends around the periphery of a feminine hygiene pad. In other embodiments, the resilient reinforcing member may only be present in the periphery of the center or crotch portion of the pad. The strength and flexibility required of the reinforcing member will vary depending on the pad stiffness prior to reinforcing of the pad and the use to which the pad is to be put. The reinforcing element is a flexibly stiff, resilient, substantially nonelastic material. The reinforcing element material may be deformed and then is springy and will return to its shape after deformation.

10 Claims, 7 Drawing Sheets

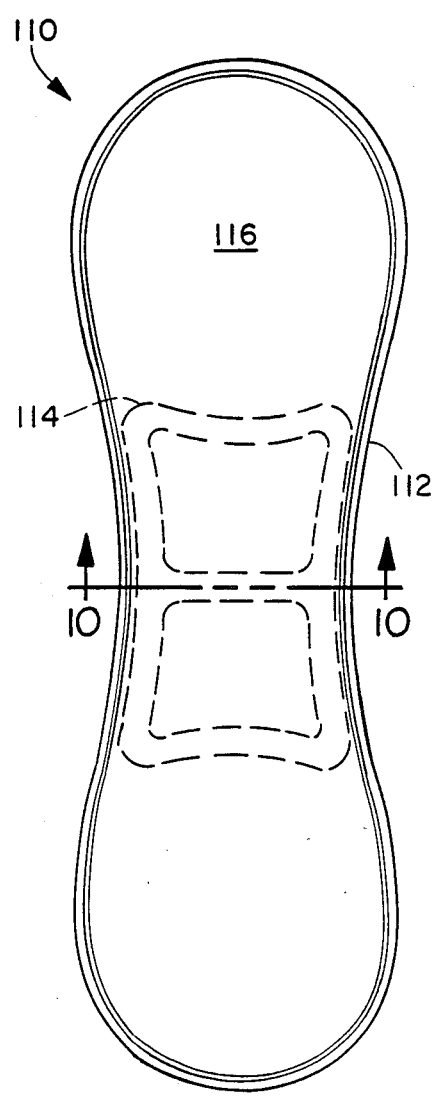
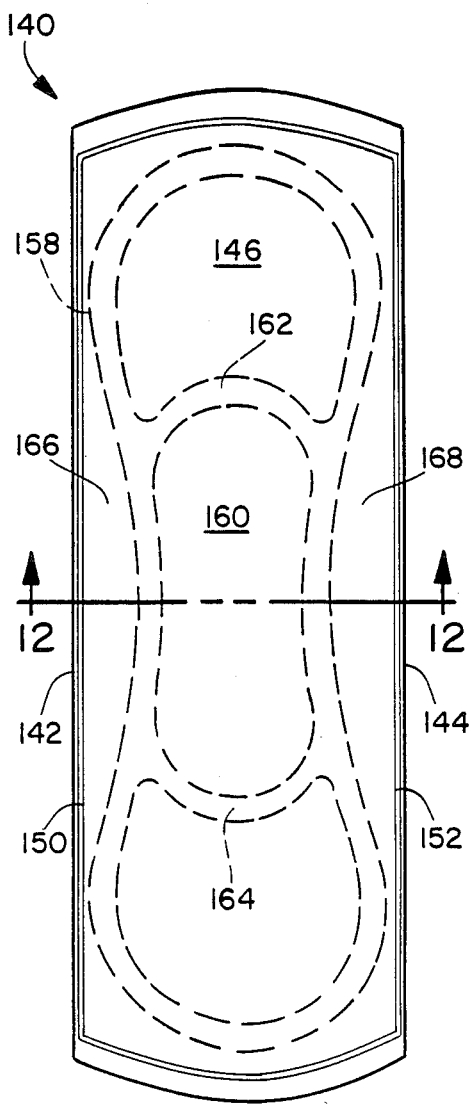
FIG. 9
FIG. 11
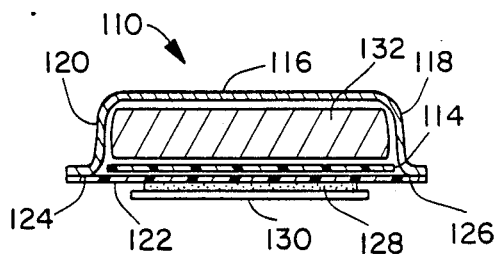
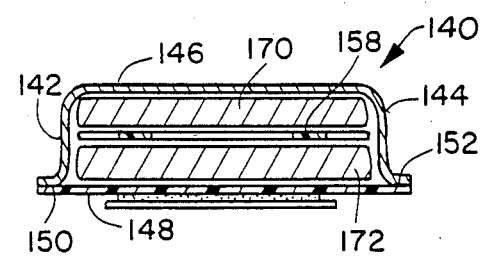
FIG. 10
FIG. 12

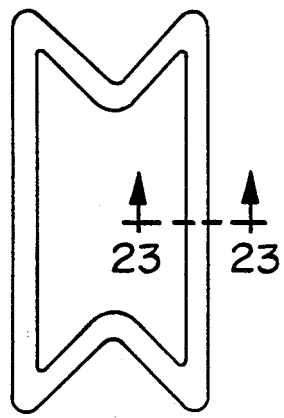
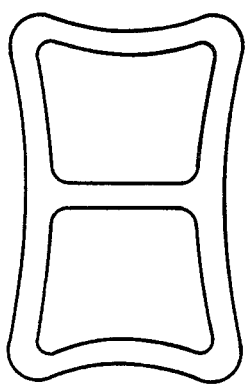
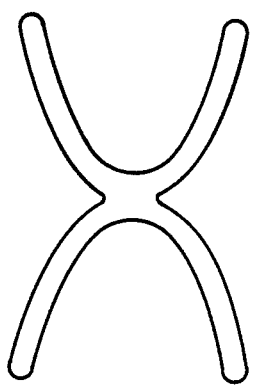
FIG. 15  FIG. 16  FIG. 17
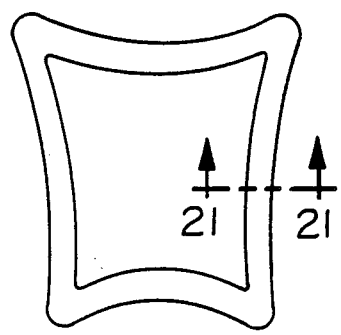
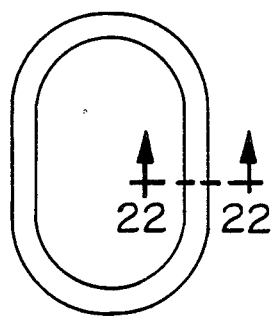
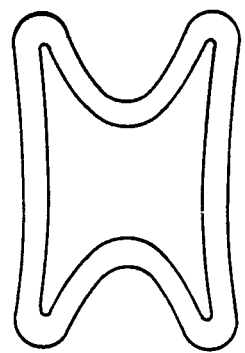
FIG. 18  FIG. 19  FIG. 20
FIG. 21  FIG. 22  FIG. 23

ABSORBENT PAD WITH REINFORCING MEMBER TO RESIST DEFORMATION

This application is a continuation of U.S. Ser. No. 07/069,690 filed July 6, 1987.

TECHNICAL FIELD

This invention relates to products for absorption of human exudate. It particularly relates to catamenial pads, diapers, incontinent garments or wound dressings.

BACKGROUND ART

In the formation of pads for absorption of human exudate, the pads are commonly formed with a liquid-permeable bodyside member, an absorbent center section and a liquid-impermeable backing sheet or baffle. These pads, whether utilized as diapers, incontinent garments or feminine pads, all are subject to failure by leaking. While leaking may have several causes, such as an exhaustion of the absorbent capacity of the absorbent member, misplacement of the pad or inability to handle sudden surges of fluid, one common cause of leakage is the bending and twisting of the pad due to body movement of the wearer which deforms the pad such that it is no longer properly placed to absorb fluids.

To overcome the problem of the pads becoming misplaced, one solution has been to provide elasticized edges that will bear against the sides of the wearer. Earlier devices have relied on belts, support garments or underwear to hold the absorbent pads in place It is proposed in U.S. Pat. No. 3,570,493—Olsson that an elastic deformable member be provided in the sanitary napkin that will be deformed when the pad is worn and urge the edges of the pad against the legs of the wearer.

Another method of preventing leakage has been to extend wings from the edge of the pad, such as disclosed in U.S. Pat. No. 4,589,876—Van Tilburg, that aid in holding the pad in place by wrapping around the crotch section of the panty of the wearer. However, such pads are inconvenient to use and still are subject to bending and twisting during wearing by which they become permanently deformed. It has been proposed in European Patent Application No. 0,140,470 to provide a pad with a boat-shaped foam backing member that is resilient. However, such pads are bulky and remain subject to permanent deformation during wearing.

Therefore, there remains a need for a shaped pad for absorption of human exudate that will return to its desired shape after it has been deformed or twisted during wearing. Further, it is desirable that the pads return to shape even when wet or after being deformed for a lengthy period of time.

DISCLOSURE OF THE INVENTION

The object of this invention is to overcome disadvantages of prior absorbent pads.

An additional object of this invention is to provide a pad for absorption of human exudate that will return to shape after bending or twisting.

A further object is to provide a pad that resists bending and twisting.

Another object is to provide a feminine pad that will leak less.

These and other objects of the invention are generally accomplished by providing a flexibly stiff reinforcing member that will maintain the shape of a pad for absorption of human exudate during use. Further, the flexibly stiff reinforcing member will return the pad to its desired shape, even after it has been deformed by movement of the wearer. In a particularly preferred form, the flexibly stiff reinforcing member is a flat strip of polyethylene that extends around the periphery of the pad. In other embodiments, the resilient reinforcing member may only be present in the periphery of the center or crotch portion of the pad. The strength and flexibility required of the reinforcing member will vary depending on the pad stiffness prior to reinforcing of the pad and the use to which the pad is to be put. The reinforcing element is a flexibly stiff, resilient, substantially nonelastic material. The material may be deformed and then is springy and will return to its shape, after deformation.

BRIEF DESCRIPTION OF THE DRAWINGS

FIG. 9 is a top view of an hourglass-shaped pad in accordance with the invention having a reinforcing element in the crotch portion.

FIG. 10 is a cross-sectional view of the pad of FIG. 9 on cross-sectional line 9—9 of FIG. 9.

FIG. 11 is a top view of a pad in accordance with the invention in which a flat rectangular pad is provided with an hourglass-shaped reinforcing element.

FIG. 12 is a cross-sectional view of the pad of FIG. 11 on cross-sectional line 2—2 of FIG. 11.

FIGS. 15, 16, 17, 18, 19 and 20 are plan views of reinforcing elements in accordance with the invention.

FIG. 21 is a cross-sectional view of the reinforcing element of FIG. 18 on cross-sectional line 8—8 of FIG. 18.

FIG. 22 is a cross-sectional view of the reinforcing member of FIG. 19 on cross-sectional line 5—5.

FIG. 23 is a cross-sectional view of the reinforcing member of FIG. 15 on cross-sectional line 7—7.

MODES FOR CARRYING OUT THE INVENTION

Figures 1, 2, 3:
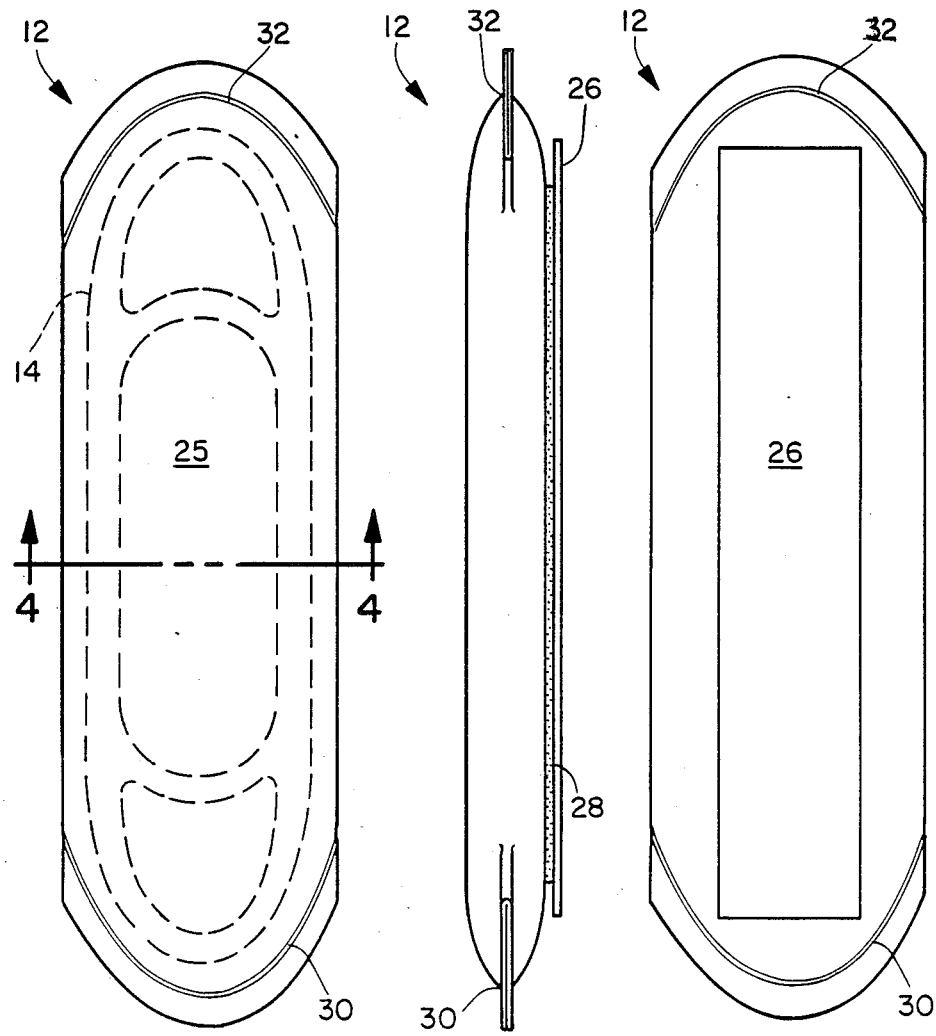
FIGS. 1, 2 and 3 are top, bottom and side views of a pad in accordance with the invention.
Figure 4:
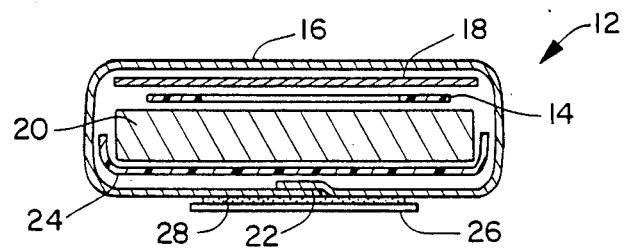
FIG. 4 is a cross-sectional view of the pad of FIG. 1 on cross-sectional line 4.

The invention has numerous advantages over prior absorbent pads. The pads resist bunching and twisting and if bunching or twisting takes place, they are able to return to the desired shape because of the flexibly stiff, resilient, substantially nonelastic reinforcing member. The reinforcing member prevents leaks as it maintains the pad in which it is located in the proper shape to present itself for absorption of exudate. The pads of the invention also are more comfortable as they maintain their desired shape and do not become dislocated or deformed so that they do not fit properly and may be used for infant diapers, adult incontinence, feminine hygiene or wound dressings. These and other advantages of the invention will be apparent from the discussion and description of the drawing.

Illustrated in FIGS. 1–4 is a generally flat pad 12 that is provided with the flexibly stiff, springy, substantially nonelastic reinforcing member 14 that extends generally around the periphery of the pad 12. The pad, as best illustrated in cross-section of FIG. 4, has a permeable bodyside member 16. Below the permeable bodyside member 16 is a bonded carded web 18. Between the bonded carded web 18 and a fluff absorbent 20 is located the reinforcing member 14. The permeable member 16 is wrapped around the pad and sealed to itself at 22 on the back of the pad. The pad is provided with a liquid-impermeable baffle 24 to prevent the flow of fluids from the bodyside 25 through the pad 12. The pad 12 further is provided with a peel strip 26 that covers a garment attachment adhesive 28. The pad 12 is provided with end seals 30 and 32 that may be sealed by heat sealing or adhesives.

Figure 5:
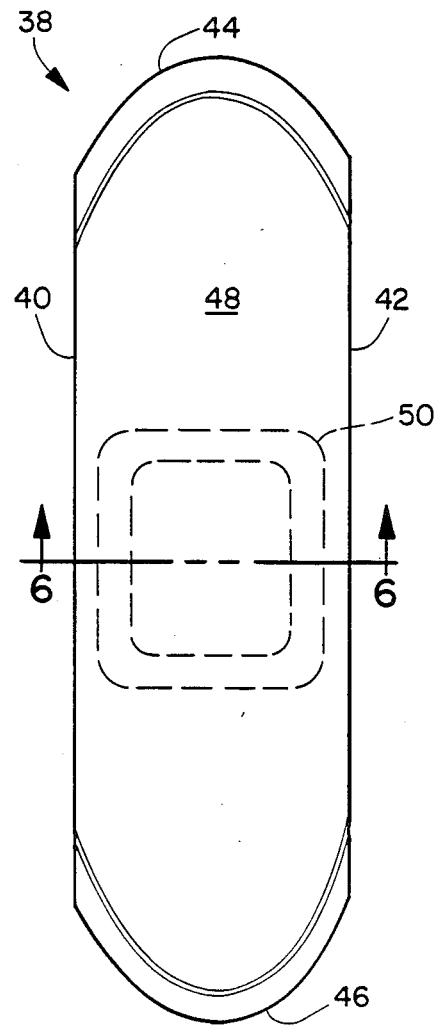
FIG. 5 is a top view of a pad in accordance with the invention with a reinforcing member in the crotch portion.
Figure 6:
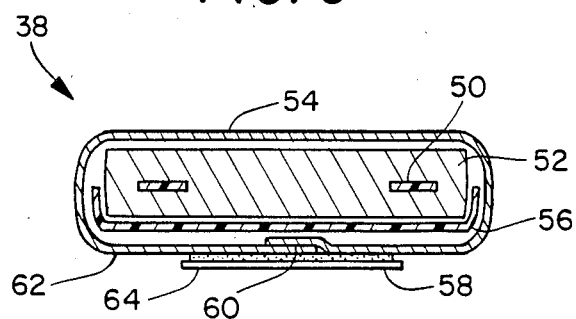
FIG. 6 is a cross-sectional view of the pad of FIG. 5 on cross-sectional line 6—6 of FIG. 5.

Illustrated in FIGS. 5 and 6 is a feminine pad 38 that, as shown in the top view of FIG. 5, is a generally rectangular pad having rounded ends and parallel sides 40 and 42. The pad 38 has ends 44 and 46. The center or crotch portion of the bodyside 48 is provided with a flexibly stiff, springy, substantially nonelastic reinforcing member 50. As illustrated in FIG. 6, the reinforcing member 50 is embedded in the absorbent 52 of pad 38. The pad is of conventional construction, having a permeable member on the bodyside that is wrapped around the entire pad, including baffle 56, and joined at 60 where it overlaps. The back of the pad 62 has a garment attachment adhesive 58 that is protected by peel strip 64 until the pad is to be used. The reinforcing member 50 is located in the crotch section 48 of the pad and extends generally to the peripheral portions of the absorbent. By placing the reinforcing member 50 only in the crotch section 48, it will maintain the shape of the pad in the area where shape retention is most desired and minimize any stiffness of the pad in the ends. Further, the embedding of the reinforcement element 50 in the absorbent 52 also minimizes any chafing or discomfort caused by the flexibly stiff, resilient, springy reinforcing member contacting the legs of the wearer.

Figure 7:
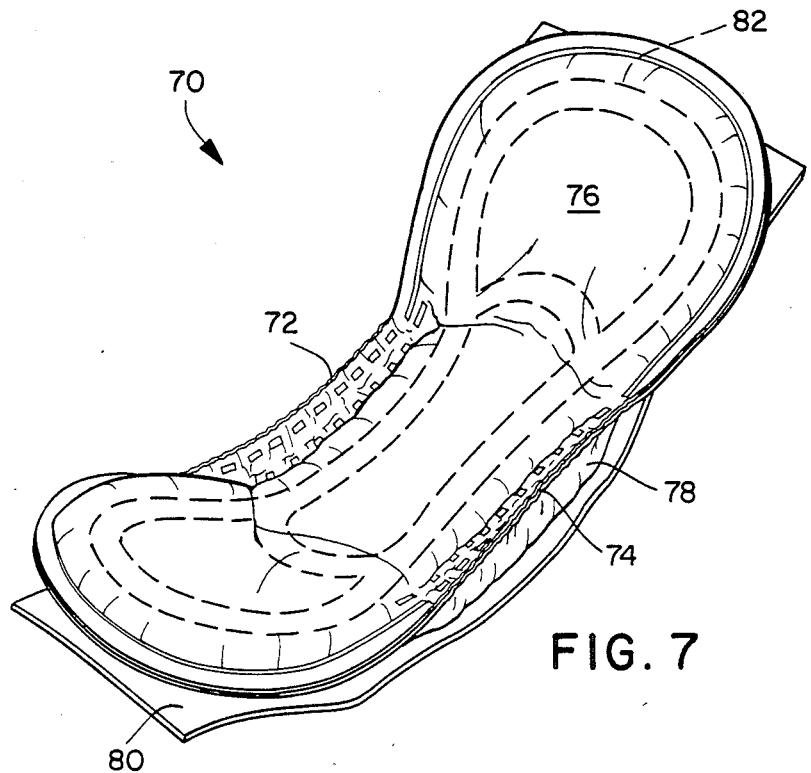
FIG. 7 is a perspective view of a curved pad in accordance with the invention.

FIG. 7 illustrates a curved pad 70 for incontinence or catamenial use. The pad is provided with elasticized edges 72 and 74 to aid in sealing the pad to the wearer in the crotch region. The pad has a permeable bodyside member 76 and an impermeable back 78. The pad 70 further is provided with a garment attachment adhesive, not shown, that is protected by peel strip 80 prior to use. The pad is provided with a peripheral reinforcement member 82 that serves to help shape the pad as well as return the pad to shape after it is deformed. The peripheral reinforcement member 82 is shaped in a curved shape.

Figure 8:
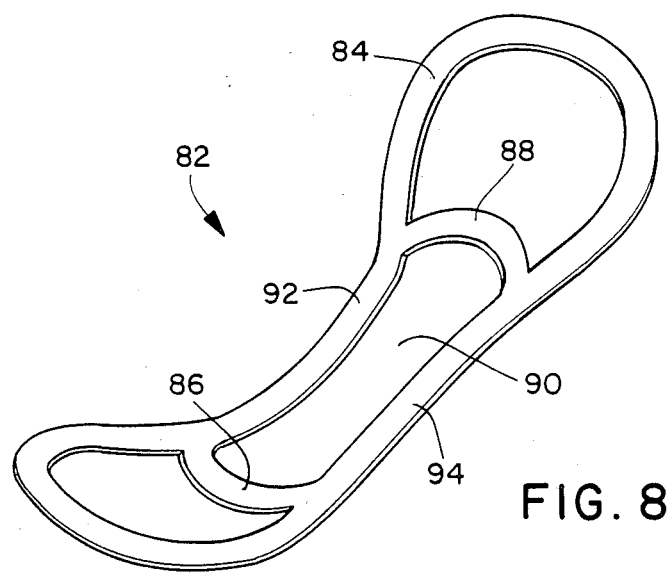
FIG. 8 is a perspective view of the reinforcing element of the pad of FIG. 7.

FIG. 8 illustrates the reinforcing member 82 of pad 70. The reinforcing member is a thin, flexibly stiff, springy, substantially nonelastic member that has a peripheral section 84. The reinforcing member 82 as shown is provided with cross-reinforcing members 86 and 88. By controlling the location of the cross members 86 and 88, the way the reinforcing member deforms during use may be controlled. For instance, by location as shown, the crotch region will collapse under pressure quite easily, but will return to shape after the pressure is released. This is because there are no cross-reinforcing members in the crotch section 90 and, therefore, the peripheral crotch sections 92 and 94 may easily collapse.

FIGS. 9 and 10 illustrate another pad 110 of the invention. In the top view of the pad 110 of FIG. 9, the pad has a general hourglass shape with a narrowed crotch portion 112 where a reinforcing member 114 is located. The pad 110 is shown in cross-section in FIG. 10. The pad is provided with a bodyside permeable member 116 that extends down the sides 118 and 120 to be attached adhesively or by heat to the liquid-impermeable backing baffle 122 in areas 124 and 126. The pad is provided with a body attachment adhesive 128 that is protected by a peelable strip 130 prior to use. As shown in FIG. 10, the reinforcing member 114 of this rectangular cross-section is placed below absorbent 132.

FIGS. 11 and 12 illustrate a generally flat feminine or incontinence pad 140. The pad 140 has sides 142 and 144. The pad has a bodyside member 146, and as shown in the cross-sectional view of FIG. 12, a liquid-impermeable backing member 148 that is sealed to the permeable member 146 at edges 150 and 152. The pad is provided with the flexibly stiff, springy, reinforcing member 158. The reinforcing member is generally hourglass in shape with the peripheral edges of the member 158 extending somewhat farther from the edges 142 and 144 in the crotch section 160. The flexibly stiff reinforcing member is provided transverse reinforcing members at 162 and 164 to reinforce the narrowed crotch section somewhat. The structure would allow collapse of the pad easily in the unreinforced crotch areas 166 and 168 until the reinforcing member 158 was reached in the narrowed crotch section 160. The reinforcing member 158 as shown in FIG. 12 is located between two absorbent layers 170 and 172. Placement between the two reinforcing layers tends to shield the reinforcing member 158 so that the wearer does not feel the reinforcing member when the pad is deformed.

Figures 13, 14:
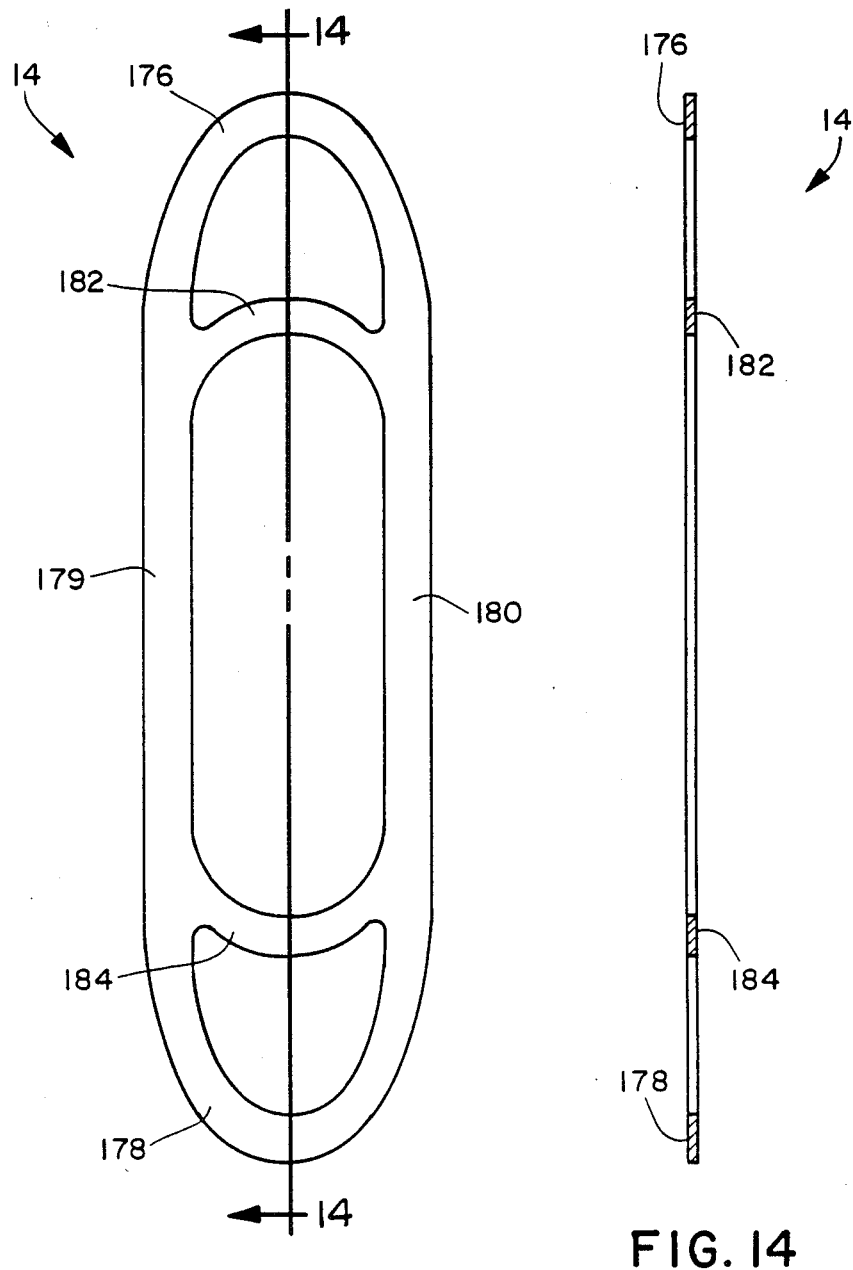
FIG. 13 is a top view of a flexibly stiff, resilient, shape-retaining reinforcing member of the invention.
FIG. 14 is a cross-sectional view of the reinforcing member of FIG. 13 on cross-sectional line 3—3 of FIG. 13.

FIGS. 13 and 14 are a top view and a cross-section view of a preferred reinforcing element 14 of the invention. The element 14 is such as that shown in the pad of FIGS. 1–4. The element 14 is a thin polymer with rounded ends 176 and 178. The crotch portion has peripheral pieces 179 and 180 but no transverse reinforcing members. Towards the ends there are cross-reinforcing members 182 and 184 that aid the member in returning to shape if the crotch portion of the reinforcing member 14 is deformed as it is worn.

FIGS. 15, 16, 17, 18, 19 and 20 illustrate various shapes of reinforcing members. The reinforcing members shown in these figures are generally the shape that would be utilized in a crotch reinforcement rather than reinforcement of the periphery of the entire pad. However, by changing the members to make them longer rather than the more square outline shown, these shapes can be used as a peripheral reinforcement for a longer rectangular pad. As shown in the cross-sectional FIG. 21 taken on line 8—8 of FIG. 18, the reinforcing members preferably have a thin rectangular cross-section. However, as shown in FIG. 22, that is a cross-section of FIG. 19 on line 5—5, the reinforcing members may have a round cross-section. The reinforcing members also may be tubular as shown by FIG. 23, which is a cross-sectional view on line 7—7 of FIG. 15. The thin, flat members are preferred as they are less obtrusive in the design of the pad.

Figure 24:
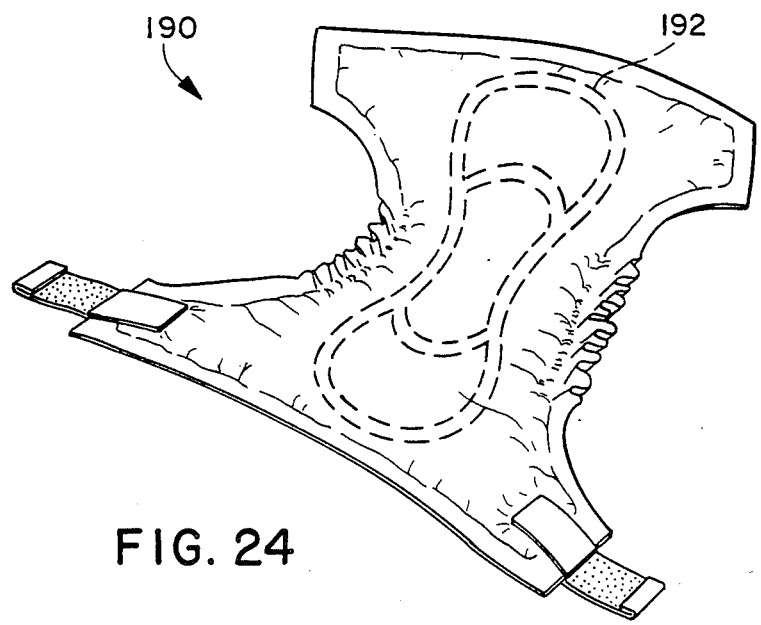
FIG. 24 is a perspective view of a diaper having a reinforcing element in accordance with the invention.

FIG. 24 is a perspective view of a diaper 190 that is provided with a reinforcing element 192 that aids in shaping of the diaper to best absorb exudate and returns the diaper to shape after the diaper is deformed. The flexibly stiff, springy reinforcing member 192 may be either formed in a curved shape, as shown, such that the crotch of the diaper is in the general shape for use or may be flat and bent with the diaper as the diaper is placed on the infant.

Figure 25:
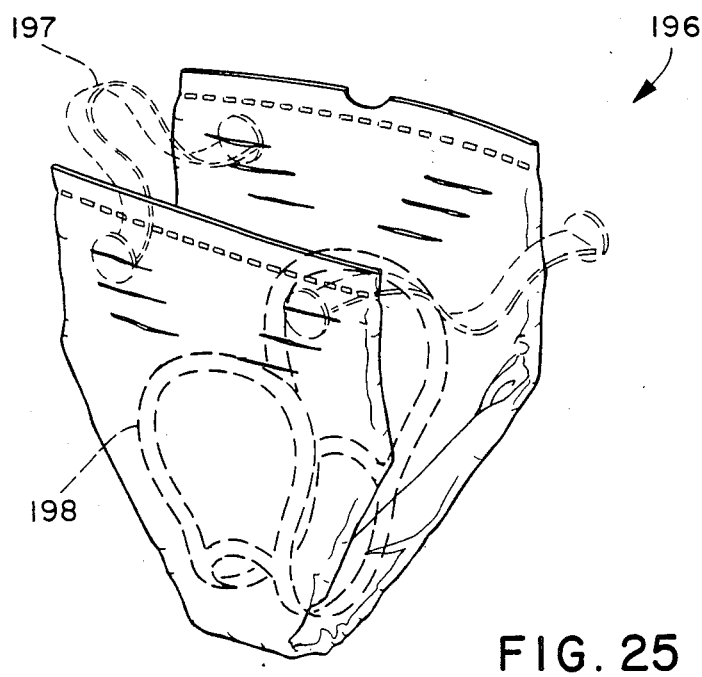
FIG. 25 is a perspective view of an incontinent garment having a reinforcing element in accordance with the invention.

FIG. 25 illustrates an incontinent garment 196 that is provided with a reinforcing member 198 in accordance with the invention. The incontinence garment 196 is designed to be held in place by straps 197 that extend upward around the hips after the garment 196 is in place. The reinforcing element 198 helps to maintain the garment in the best shape for trapping and absorption of urine and feces.

The reinforcing member of the invention may be located anywhere in the pad that will aid in the performance of the pad by maintaining the shape of the pad to be most effective. The reinforcing element may be located only in the crotch section or may extend generally coextensively with the absorbents of the pad. Further, it is possible that the reinforcing member could be located outside of the absorbent and provide peripheral shaping of the pad. Generally it is preferred that the reinforcing member be of slightly less width than the absorbent and that it be flat and generally extend around the periphery of the pad slightly within the absorbent. It is preferred that it not extend as close to the edge of the pad as the absorbent in order to shield the wearer of the pad from being able to feel the reinforcing member which might be uncomfortable. While it is generally desired that the support element be located near the periphery of the pad, it also may be provided with cross pieces across the pad in some areas. The cross-bracing would serve to aid the reinforcing member in returning to its original shape after deformation. However, the reinforcing members would be located so as to not noticeably cause discomfort during movement by the wearer. Therefore, in a preferred form, the crotch portion is not provided with cross-reinforcing members while parts of the reinforcing member at the periphery of the crotch portion of the pad may be provided with transverse members to aid in returning the crotch portion to its original effective shape after deformation. The reinforcing member 14 of FIGS. 1-4 and FIGS. 13 and 14 are illustrations of this type of preferred reinforcing member. The reinforcing member of FIGS. 7 and 8 also is illustrative of this method wherein the crotch is not cross-reinforced while the reinforcing member does have some cross-bracing in the regions that border the crotch.

The peripheral reinforcing element of the invention may be formed of any material that provides the desired improvement in shape-retaining properties in a particular pad. The materials generally are flexibly stiff, springy, shape-retaining and substantially nonelastic. The reinforcing materials also may be described as willowy in that they will bend by a great amount under pressure but then will return to their original shape when pressure is released. The material forming the reinforcing element may be any desired material having these properties. Typical of such materials are spring wire, plastic-coated spring steel wire and polymer, members either in flat or other cross-section. A preferred material is a middle-density polyethylene of between about 0.005 and about 0.03 inches which, in a fluff-based feminine pad, has been found to increase the ability of the pad to resist bunching and twisting without causing abrasion or discomfort to the wearer. Other polymers that have been found suitable are other high- and low-density polyethylenes as well as polypropylene and polystyrene copolymers. The reinforcing and shaping elements may also be formed by being cast, printed or molded in place on one of the layers of the absorbent product. The casting or extrusion of a hardenable resin in place to form the reinforcing member during manufacture is a method allowing forming the reinforced pad in a continuous manner.

It has been found that, when the reinforcing elements are utilized in curved pads, the pads have an improved tendency to conform to the body and are less likely to become displaced than pads that are shaped solely by elastic. The curved preshaped feminine pads of the invention are able to stay in place satisfactorily without the use of adhesives or other fastening or support system. The hourglass shape reinforcing insert is particularly preferred as staying in place without adhesive. The response of the hourglass peripheral support to the pinching action between the legs forces the ends of the hourglass to push towards each other. This is believed to occur because of the hourglass shape in combination with the two cross-bridging components such as 162 and 164 in the embodiment of FIG. 11. The rectangular cross-section of the preferred embodiments of the preferred reinforcing elements, such as FIGS. 8 and 11, are also believed to aid in pulling the elements toward each other. The polymer films may be cut from flat sheets of polymer and then heat-shaped to the desired curve prior to placement in the pad.

As illustrated in the drawings attached, the reinforcing element may be placed in any suitable position within the pad. Generally, it is preferred that the reinforcing element be below at least part of the absorbent in order to minimize any discomfort or feel that is associated with the use of the flexibly stiff reinforcing member. By placing the reinforcing member either below the absorbent or in the absorbent, the tendency to chafe the legs of the wearer or to cause discomfort is minimized. It is even possible to place the reinforcing element on the outside of the liquid-impermeable backing member by adhesive connection to the outside of the baffle.

The absorbent utilized in the pads of the invention may be any material that provides sufficient absorption to give the pad utility for its intended use. Pads for incontinence use are required to absorb far larger quantities of urine and feces than diapers. Further, diapers are required to have a larger absorbent capacity than feminine pads. Further, the absorbents utilized in feminine pads may have somewhat different properties as the menstrual fluid has different properties than urine. Typical of suitable materials are wood fluff, coform (an air-formed mixture of meltblown polypropylene and devilicated wood fibers), polyesters and meltblown polypropylene. It is also possible that the absorbent may contain superabsorbent sheets or particles whose use is well known in the formation of diapers and incontinence garments.

The liquid-permeable cover member may be any of the known materials suitable for use in pads for absorption of human exudate. Typical of such materials are spunbonded materials, perforated polymer sheets, tissue and woven fabrics. A preferred material is spunbonded polypropylene as it is low in cost and provides good fluid transmission.

The impermeable baffle that forms the backing of the typical pad of the invention may be any desired material. The material may be vapor permeable and liquid-impermeable. Typical of such materials are films of polypropylene and polyethylene.

While the pads of the invention have been shown in flat and curved form, it is possible that the flexibly stiff, resilient, springy reinforcing members of the invention may be utilized to form the pad in more complicated shapes. Pads with the reinforcing element of the invention are particularly suitable for this type of formation as the formation of absorbent material such as wood fluff into permanent three-dimensional shapes is difficult and expensive.

The foregoing description is not intended to be exhaustive of all possible embodiments of the invention. It is understood by those skilled in the art that many variations are possible while still remaining within the scope of this invention. It would be obvious to one of ordinary skill in the art that the invention would include embodiments not shown. For instance, the reinforcing element of the invention, rather than being made up of a single member, could be formed of several members that, in cooperation, result in the benefit of the invention.

The scope of the invention is only intended to be limited by the scope of the claims attached hereto.

We claim:

1. A device for absorption of human exudate comprising an absorbent, a liquid permeable cover and a liquid-impermeable baffle cooperating to enclose said absorbent, and reinforcing means for shaping said device to conform to the body of a user, said reinforcing means having a predetermined arcuate shape prior to being assembled thereby imparting a cup-like shape to said device.

2. A device for absorption of human exudate comprising an absorbent, a liquid permeable cover and a liquid-impermeable baffle cooperating to enclose said absorbent, and reinforcing means for shaping said device to conform to the body of a user, said reinforcing means being a non-apertured member having a predetermined arcuate shape prior to being assembled thereby imparting a cup-like shape to said device.

3. A device for absorption of human exudate comprising an absorbent, a liquid permeable cover and a liquid-impermeable baffle cooperating to enclose said absorbent, and a reinforcing member having three or more axially aligned openings formed therein with the end openings being smaller than the opening aligned therebetween.

4. A device for absorption of human exudate comprising an absorbent, a liquid permeable cover and a liquid-impermeable baffle cooperating to enclose said absorbent and reinforcing means for shaping said device to conform to the body of a user, said reinforcing means having a hollow tubular cross-section with semicircular shaped ends.

5. The device of claim 4 wherein said reinforcing means is arcuate in shape.

6. The device of claim 5 wherein said reinforcing means has a predetermined arcuate shape prior to being assembled thereby imparting a cup-like shape to said device.

7. A device for absorption of human exudate comprising an absorbent, a liquid permeable cover and a liquid-impermeable baffle cooperating to enclose said absorbent, and reinforcing means for shaping said device to conform to the body of a user, said reinforcing means being a relatively flat non-apertured member having at least one outwardly extending arm, said arm having a rounded end.

8. The device of claim 7 wherein said reinforcement member has at least two outwardly extending arms, each of said arms having a rounded end.

9. The device of claim 7 wherein said reinforcing member has at least three outwardly extending arms, each of said arms having a rounded end.

10. The device of claim 7 wherein said reinforcing member has at least four outwardly extending arms, each of said arms having a rounded end.

* * * * *